United States Patent
Pataut et al.

(10) Patent No.: US 7,157,076 B2
(45) Date of Patent: Jan. 2, 2007

(54) AEROSOL DEVICE COMPRISING A HAIR TREATMENT COMPOSITION, AND HAIR TREATMENT PROCESS

(75) Inventors: Francoise Pataut, Paris (FR); Francois Le Bourhis, Aubervilliers (FR)

(73) Assignee: L'Oreal, Paris (FR)

( * ) Notice: Subject to any disclaimer, the term of this patent is extended or adjusted under 35 U.S.C. 154(b) by 150 days.

(21) Appl. No.: 10/447,229

(22) Filed: May 29, 2003

(65) Prior Publication Data

US 2004/0047812 A1   Mar. 11, 2004

Related U.S. Application Data

(60) Provisional application No. 60/385,558, filed on Jun. 5, 2002.

(30) Foreign Application Priority Data

May 31, 2002   (FR) .................................. 02 06734

(51) Int. Cl.
*A61K 8/00*   (2006.01)
(52) U.S. Cl. .................... 424/47; 424/70.1; 424/70.12; 222/389
(58) Field of Classification Search ................ 222/105, 222/386.5, 389, 130, 402.1–402.25; 424/47, 424/70.1, 70.9, 70.11–70.12, 70.22, 70.27, 424/70.31
See application file for complete search history.

(56) References Cited

U.S. PATENT DOCUMENTS

| | | | | |
|---|---|---|---|---|
| 4,638,822 A * | 1/1987 | Grollier et al. | ............. | 132/209 |
| 4,839,168 A * | 6/1989 | Abe et al. | ...................... | 424/74 |
| 5,839,623 A * | 11/1998 | Losenno et al. | ......... | 222/402.1 |
| 5,915,598 A * | 6/1999 | Yazawa et al. | .......... | 222/402.1 |
| 6,016,934 A | 1/2000 | Moriguchi | | |
| 6,113,070 A * | 9/2000 | Holzboog | ................... | 251/342 |
| 6,131,776 A | 10/2000 | De Laforcade et al. | | |
| 6,230,762 B1 | 5/2001 | Baudin et al. | | |
| 6,244,475 B1 * | 6/2001 | Walz et al. | ................. | 222/387 |
| 6,509,023 B1 * | 1/2003 | Branlard et al. | ............ | 424/401 |
| 6,548,050 B1 * | 4/2003 | Bara | .......................... | 424/64 |
| 2001/0015359 A1 | 8/2001 | Benoist | | |

FOREIGN PATENT DOCUMENTS

| | | |
|---|---|---|
| EP | 0 972 723 | 1/2000 |
| EP | 0972 723 A2 | 1/2000 |
| EP | 0 990 599 | 4/2000 |
| FR | 2 677 619 | 12/1992 |
| JP | S32-1573 | 1/1957 |
| JP | 5184422 | 7/1992 |
| JP | A-H10-287380 | 10/1998 |
| JP | A-2000-024557 | 1/2000 |
| JP | 2000-109148 | 4/2000 |
| JP | 2000-264812 | 9/2000 |
| JP | 2002-509020 | 3/2002 |
| WO | WO 99/36169 | 7/1999 |

OTHER PUBLICATIONS

Shepperd, AEROSOLS: Science and Technology, 1961, Interscience Publishers, p. 21.*
U.S. Appl No. 10/449,083, filed Jun. 2, 2003, Le Bourhis.
Notice of Reasons for Rejection (w/English translation of Japanese Patent Office Rejection mailed Nov. 15, 2005).

* cited by examiner

*Primary Examiner*—Frederick C. Nicolas
(74) *Attorney, Agent, or Firm*—Oblon, Spivak, McClelland, Maier & Neustadt, P.C.

(57) ABSTRACT

The present invention relates to a two-compartment aerosol device containing a hair treatment composition in a first compartment and a compressed gas chosen from air, nitrogen and carbon dioxide, and mixtures thereof, in a second compartment, where the hair treatment composition contains, in an alcoholic or aqueous-alcoholic cosmetically acceptable medium, at least one hair sheen agent and/or conditioner in a concentration of greater than 0.4% by weight relative to the total weight of the composition.

22 Claims, No Drawings

AEROSOL DEVICE COMPRISING A HAIR TREATMENT COMPOSITION, AND HAIR TREATMENT PROCESS

REFERENCE TO PRIOR APPLICATIONS

This application claims priority to U.S. provisional application No. 60/385,558 filed Jun. 5, 2002, and French patent application 0206734 filed May 31, 2002, both incorporated herein by reference.

SUMMARY OF THE INVENTION

The present invention relates most generally to an aerosol device comprising a hair treatment composition, and a hair treatment process where the composition is applied to hair from the device. In a preferred embodiment the device is a two-compartment device. For simplicity, this two-compartment device is referred to in the following description of the invention, but the invention is not limited thereto. For example, the device may have more than two compartments.

DETAILED DESCRIPTION OF THE PREFERRED EMBODIMENTS AND BACKGROUND OF THE INVENTION

The present invention relates to a two-compartment aerosol device comprising a hair treatment composition and a particular compressed gas, and to a hair treatment process.

Hair treatment compositions, packaged in aerosol spray form, generally contain a liquid phase comprising, in an alcoholic or, less commonly, aqueous-alcoholic cosmetically acceptable medium, a hair treatment agent, for example an agent for giving the hair sheen and/or a hair conditioner, and a propellant, which is a liquefied gas under reduced pressure or dissolved in the liquid phase.

Other aerosol devices comprising such a liquid phase exist, but they comprise compressed gases for propelling the liquid phase. However, these compressed-gas devices have the drawback of losing gas pressure over time. Specifically, it is observed that the compressed gases leak out over time or during poor use of the container, i.e. when it is held upside down.

This drawback results in poor propulsion of the liquid phase and, consequently, poor distribution of the liquid phase on the hair.

The Applicant has made the surprising discovery that mechanical separation of the alcoholic or aqueous-alcoholic liquid phase from the propellent compressed gas makes it possible to solve these problems of leakage and of distribution of the liquid phase on the hair. In addition, the use of a two-compartment aerosol device with a particular compressed gas makes it possible to obtain a gentle and broad spray, which ensures improved distribution of the liquid phase on the hair, disturbs the hairstyle less and maintains the shape of the said hairstyle.

One subject of the invention is thus a two-compartment aerosol device comprising a hair treatment composition and a compressed gas as described below.

Another subject of the present invention consists of a hair treatment process.

Other subjects, characteristics, aspects and advantages of the invention will emerge even more clearly on reading the description and the various examples that follow.

The two-compartment aerosol device according to the invention comprises:

(a) a hair treatment composition comprising, in an alcoholic or aqueous-alcoholic cosmetically acceptable medium, at least one hair sheen agent and/or conditioner in a concentration of greater than 0.4% by weight relative to the total weight of the composition, in a first compartment, and (b) a compressed gas chosen from air, nitrogen and carbon dioxide, and mixtures thereof, in a second compartment, air being particularly preferred.

The said compressed gas is preferably used at a pressure of between 1 and 12 bar and better still between 9 and 11 bar.

For the purposes of the present invention, the term "sheen agent" means any compound capable of giving the hair sheen greater than that of the hair before treatment. This sheen characteristic may be evaluated in a sensory manner or by means of suitable technical devices, for instance photogoniometers.

For the purposes of the present invention, the term "conditioner" means any compound capable of improving at least one of the cosmetic properties of the hair, such as its disentangling, softness, body or smoothness.

The hair sheen agent and/or conditioner used in the context of the present invention is chosen especially from silicones, fatty substances or other non-silicone agents known for their conditioning or sheen-providing properties, and mixtures thereof.

It is especially possible to use in the context of the present invention non-volatile silicone oils such as polydimethylsiloxanes (PDMS), phenylated polyorganosiloxanes such as phenyltrimethicones, phenyltrimethylsiloxydiphenylsiloxanes, diphenylmethyldimethyltrisiloxanes, diphenyldimethicones, phenyldimethicones and polymethylphenylsiloxanes, which may be fluorinated; polysiloxanes modified with fatty acids, with fatty alcohols or with polyoxyalkylenes, fluorosilicones and perfluorinated silicone oils, and mixtures thereof.

Among the preferred non-volatile silicone oils that may be mentioned are polydimethylsiloxanes, polymethylphenylsiloxanes, silicones comprising polyoxyalkylene blocks or grafts, in particular polyoxyethylene or copoly (oxyethylene/oxypropylene) blocks or grafts such as dimethicone copolyols, silicones comprising both hydrocarbon-based hydrophobic groups (for example $C_2$–$C_{30}$ alkyl groups) and polyoxyethylenated or copoly (oxyethylenated/oxypropylenated) blocks or grafts such as alkyldimethicone copolyols, silicones bearing fluoro or perfluoro groups such as perfluoroalkyl polydimethylsiloxanes and perfluoroalkyl polymethylphenylsiloxanes, and mixtures thereof.

These oils may be silicone oils optionally comprising alkyl or alkoxy groups at the end of the silicone chain or pendant thereon.

As volatile silicone oils that may be used in the invention, mention may be made of linear or cyclic silicones, preferably with a viscosity at room temperature and at atmospheric pressure of less than 8 mm$^2$/s (8 cSt), and in particular comprising from 2 to 7 silicon atoms. Mention may be made especially of octamethylcyclotetrasiloxane, decamethylcyclopentasiloxane, hexadecamethylcyclohexasiloxane, heptamethylhexyltrisiloxane and heptamethyloctyltrisiloxane, and mixtures thereof.

Hydrocarbon-based oils may also be used in the context of the present invention as sheen agents and/or conditioners.

The term "hydrocarbon-based oil" means an oil predominantly containing carbon and hydrogen atoms and especially alkyl or alkenyl chains, for instance alkanes or alkenes, but also an oil containing, in addition to hydrogen and carbon atoms, oxygen atoms in the form of an ether, ester, alcohol or carboxylic acid function.

Mention may thus be made of hydrocarbon-based oils such as liquid paraffin or liquid petroleum jelly, mink oil, turtle oil, soybean oil, perhydrosqualene, sweet almond oil, beauty-leaf oil, palm oil, grapeseed oil, sesame oil, corn oil, parleam oil, arara oil, rapeseed oil, sunflower oil, cotton oil, apricot oil, castor oil, avocado oil, jojoba oil, olive oil or cereal germ oil; esters of lanolic acid, of oleic acid, of lauric acid and of stearic acid, fatty esters, such as isopropyl myristate, isopropyl palmitate, butyl stearate, hexyl laurate, diisopropyl adipate, isononyl isononanoate, 2-ethyhexyl palmitate, 2-hexyldecyl laurate, 2-octyldecyl palmitate, 2-octyldodecyl myristate or lactate, bis(2-ethylhexyl) succinate, diisostearyl malate, glyceryl triisostearate or diglyceryl triisostearate; higher fatty alcohols containing at least 12 carbon atoms, such as stearyl alcohol or oleyl alcohol, linoleyl alcohol linolenyl alcohol, isostearyl alcohol or octyldodecanol.

Waxes may also be used as sheen agents and/or conditioners. These waxes may be of natural origin (carnauba wax or candelilla wax) or of synthetic origin, such as silicone waxes, synthetic ceramides or natural ceramides.

Linear or branched fatty alcohols comprising from 10 to 30 carbon atoms may also be used as sheen agents and/or conditioners.

Among the sheen agents and/or conditioners mentioned above, the ones preferably used are phenylated polyorganosiloxanes, liquid petroleum jelly, isopropyl myristate and isopropyl palmitate, or mixtures thereof.

The said hair sheen agent and/or conditioner is preferably present in an amount of between 0.4% and 40% by weight and better still between 1% and 20 by weight, relative to the total weight of the hair treatment composition, limits included.

The term "cosmetically acceptable medium" means a medium that is compatible with the hair, but which also has a pleasant odour, appearance and feel.

The alcoholic or aqueous-alcoholic cosmetically acceptable medium comprises at least one alcohol such as a $C_{1-4}$ alcohol, for example ethanol or isopropanol.

In an aqueous-alcoholic medium, the proportion of water may range between 1% and 95% and preferably between 15 and 90% of the total weight of the aerosol composition.

The hair treatment composition may also comprise additives such as nonionic, cationic, anionic or amphoteric fixing polymers, treating active agents, moisturizers such as glycerol, UV-screening agents, acids, bases, plasticizers, solubilizers, preserving agents, colorants, pigments, fragrances, vitamins, provitamins, nonionic, anionic, cationic or amphoteric surfactants and anticorrosion agents, and mixtures thereof.

A person skilled in the art will take care to select the optional additives and the amount thereof such that they do not harm the properties of the compositions of the present invention.

These additives are especially present in the composition according to the invention in an amount ranging from 0% to 20% by weight relative to the total weight of the composition.

Preferably, the two-compartment aerosol device consists of an outer aerosol can comprising an inner pocket hermetically welded to a valve. The composition is introduced into the inner pocket and a compressed gas is introduced between the pocket and the can at a pressure that is sufficient to eject the product in the form of a spray through the orifice of a nozzle. Such a device is sold under the name EP Spray by the company EP-Spray System SA.

The aerosol devices of the invention may preferably be hair lacquers.

The present invention also relates to a hair treatment process, which consists in vaporizing the hair treatment composition contained in the aerosol device according to the invention onto wet or dry hair, and leaving the hair to dry with or without supplying external heat.

The examples that follow are given as illustrations of the present invention.

In the examples that follow, all the amounts are indicated as weight percentages relative to the total weight of the composition, except where otherwise mentioned.

EXAMPLE 1

A hair treatment composition was prepared from the ingredients below:

|  | % by weight |
| --- | --- |
| Phenyltrimethylsiloxytrisiloxane sold under the tradename 556 Cosmetic Grade Fluid by the company Dow Corning[1] | 10.00 |
| Ethylhexyl methoxycinnamate sold under the tradename Parsol ® MCX by the company Roche Vitamins | 0.05 |
| Fragrance | 0.10 |
| Absolute ethyl alcohol      qs | 100 |

The composition prepared above was introduced into the aerosol distribution device sold under the name EP Spray by the company EP Spray System SA described above. A valve of reference 6001 format D6 is attached to a standard aerosol can and the diffuser is a vortex-nozzle diffuser.

The pocket is filled with the composition as indicated above. Compressed air is introduced between the pocket and the can.

The composition was vaporized onto dry hair. The spraying takes place in the form of a gentle spray.

A very shiny head of hair is obtained after drying, without modifying the initial shape.

EXAMPLE 2

A second hair treatment composition was prepared from the ingredients below:

|  | % by weight |
| --- | --- |
| Isopropyl myristate | 4.00 |
| Liquid petroleum jelly | 4.00 |
| Ethylhexyl methoxycinnamate sold under the tradename Parsol ® MCX by the company Roche Vitamins | 0.05 |
| Fragrance | 0.10 |
| Absolute ethyl alcohol      qs | 100 |

The composition prepared above was introduced into an aerosol distribution device sold under the name EP Spray as described in Example 1.

The composition was vaporized onto dry hair.

A result very similar to that obtained in the case of Example 1 is obtained.

All references mentioned herein are incorporated herein by reference in their entirety. Where ranges or limits are discussed all endpoints are included, as are all values therewithin as if written out.

The invention claimed is:

1. An aerosol device comprising:
   (a) in a first compartment, a hair treatment composition comprising, in an alcoholic or aqueous-alcoholic cosmetically acceptable medium, at least one silicone hair sheen agent, silicone conditioner, or mixtures thereof, in a concentration of greater than 0.4% by weight relative to the total weight of the composition, and
   (b) in a second compartment, a compressed gas selected from the group consisting of air, nitrogen, carbon dioxide, and mixtures thereof.
2. A device according to claim 1, wherein the compressed gas is air.
3. The device according to claim 1, wherein the pressure of the compressed gas is from 1 to 12 bar.
4. The device according to claim 3, wherein the pressure of the compressed gas is from 9 to 11 bar.
5. The device according to claim 1, wherein the hair sheen agent, conditioner, or mixtures thereof, comprises a phenylated polyorganosiloxane.
6. The device according to claim 1, wherein the hair sheen agent, conditioner, or mixtures thereof, is present in an amount of from 0.4% to 40% by weight relative to the total weight of the composition.
7. The device according to claim 1, wherein the hair sheen agent, conditioner, or mixtures thereof, is present in an amount of from 1% to 20% by weight relative to the total weight of the composition.
8. The device according to claim 1, wherein the alcoholic or aqueous-alcoholic cosmetically acceptable medium comprises from 1 to 95% of at least one alcohol based on the total weight of said composition.
9. The device according to claim 8, wherein the alcohol is a $C_{1-4}$ alcohol.
10. The device according to claim 8, wherein the alcohol is ethanol or isopropanol.
11. The device according to claim 1, wherein the hair treatment composition further comprises at least one additive selected from the group consisting of nonionic, cationic, anionic or amphoteric fixing polymers, treating active agents, moisturizers, UV-screening agents, acids, bases, plasticizers, solubilizers, preserving agents, colorants, pigments, fragrances, vitamins, provitamins, nonionic, anionic, cationic or amphoteric surfactants, anticorrosion agents, and mixtures thereof.
12. The device according to claim 1, wherein said composition constitutes a hair lacquer.
13. The device according to claim 1, wherein said device is a two compartment device.
14. A process comprising applying the hair treatment composition contained in the aerosol device according to claim 1 from said device onto wet or dry hair, and allowing the hair to dry with or without supplying external heat.
15. The process according to claim 14, comprising vaporizing the hair treatment composition from said device onto wet or dry hair, and allowing the hair to dry with or without supplying external heat.
16. The device according to claim 1, wherein the hair sheen agent, conditioner, or mixtures thereof, comprises a polydimethylsiloxane.
17. The device according to claim 1, wherein the hair sheen agent, conditioner, or mixtures thereof, comprises a fluorosilicone.
18. The device according to claim 1, wherein the hair sheen agent, conditioner, or mixtures thereof, comprises a polyoxyalkylenated silicone.
19. The device according to claim 5, wherein the hair sheen agent, conditioner, or mixtures thereof, is present in an amount of from 1% to 20% by weight relative to the total weight of the composition.
20. The device according to claim 16, wherein the hair sheen agent, conditioner, or mixtures thereof, is present in an amount of from 1% to 20% by weight relative to the total weight of the composition.
21. The device according to claim 17, wherein the hair sheen agent, conditioner, or mixtures thereof, is present in an amount of from 1% to 20% by weight relative to the total weight of the composition.
22. The device according to claim 18, wherein the hair sheen agent, conditioner, or mixtures thereof, is present in an amount of from 1% to 20% by weight relative to the total weight of the composition.

* * * * *